United States Patent [19]
Lee et al.

[11] Patent Number: 5,354,298
[45] Date of Patent: Oct. 11, 1994

[54] SUTURE ANCHOR INSTALLATION SYSTEM

[75] Inventors: Daniel R. Lee, Warsaw; Thomas W. Sander, Winona Lake, both of Ind.

[73] Assignee: United States Surgical Corporation, Norwalk, Conn.

[21] Appl. No.: 19,149

[22] Filed: Feb. 17, 1993

Related U.S. Application Data

[63] Continuation-in-part of Ser. No. 898,799, Jun. 15, 1992, which is a continuation-in-part of Ser. No. 673,953, Mar. 22, 1991, abandoned.

[51] Int. Cl.$^5$ .............................................. A61B 17/04
[52] U.S. Cl. ...................................... 606/72; 606/139; 606/144
[58] Field of Search .................. 606/53, 60, 62, 63, 606/72, 73, 79, 86, 95, 96, 99, 104, 139, 149, 232

[56] References Cited

U.S. PATENT DOCUMENTS

| | | |
|---|---|---|
| 2,121,193 | 6/1938 | Manicke . |
| 2,381,050 | 8/1945 | Hardinge . |
| 2,490,364 | 12/1949 | Livingston . |
| 2,699,774 | 1/1955 | Livingston . |
| 3,768,635 | 10/1973 | Eggert . |
| 3,910,281 | 10/1975 | Kletschka et al. . |
| 3,951,261 | 4/1976 | Mandel et al. . |
| 4,006,747 | 2/1977 | Kronenthal et al. . |
| 4,135,623 | 1/1979 | Thyen . |
| 4,244,370 | 1/1981 | Furlow et al. . |
| 4,275,717 | 6/1981 | Bolesky . |
| 4,351,069 | 9/1982 | Ballintyn et al. . |
| 4,424,898 | 1/1984 | Thyen et al. . |
| 4,520,511 | 6/1985 | Gianezio et al. . |
| 4,550,449 | 11/1985 | Tunc . |
| 4,586,502 | 5/1986 | Bedi et al. . |
| 4,590,928 | 5/1986 | Hunt et al. . |
| 4,590,930 | 5/1986 | Kurth et al. . |
| 4,591,048 | 5/1986 | Eldridge, Jr. . |
| 4,621,640 | 11/1986 | Mulhollan et al. . |
| 4,632,100 | 12/1986 | Somers et al. . |
| 4,655,777 | 4/1987 | Dunn et al. . |

(List continued on next page.)

FOREIGN PATENT DOCUMENTS

| | | |
|---|---|---|
| 0077868 | 5/1983 | European Pat. Off. . |
| 0232049 | 1/1987 | European Pat. Off. . |
| 0241240 | 10/1987 | European Pat. Off. . |
| 0376641 | 7/1990 | European Pat. Off. . |
| 0464479 | 1/1992 | European Pat. Off. . |
| 0464480 | 1/1992 | European Pat. Off. . |
| 0465910 | 1/1992 | European Pat. Off. . |
| 3445738 | 6/1986 | Fed. Rep. of Germany . |
| 4106823 | 6/1992 | Fed. Rep. of Germany . |

(List continued on next page.)

OTHER PUBLICATIONS

Raftopoulos, "A Proposed Design for An Expanding Hip Nail," Engineering in Medicine, vol. 11 (1982), pp. 187–188.

Design News, "Ligament Fastener Cuts Recovery Time," pp. 56–57, (1989).

Instrument Makar Inc., "The Ligamentous and Capsu- (List continued on next page.)

*Primary Examiner*—Robert A. Hafer
*Assistant Examiner*—Sam Rimell

[57] ABSTRACT

The suture anchor installation system comprises a suture anchor assembly engaged with a suture anchor insertion tool. The suture anchor assembly features a two-piece suture anchor for insertion into a pre-drilled hole in a bone and at least one suture having at least one surgical needle affixed thereto. The two-piece suture anchor comprises a setting pin slidably engaged within an engagement member having barbed legs expandable in response to proximal movement of the setting pin. The suture anchor insertion tool includes a body portion and a distally extending shaft portion. An annular region of the distal end of the shaft portion engages the legs of the suture anchor engagement member. A channel in the shaft portion aligns with a channel in the body portion to accomodate the suture. Needle-retaining assemblies located on the body portion of the suture anchor insertion tool engage the surgical needle or needles attached to the suture.

15 Claims, 6 Drawing Sheets

U.S. PATENT DOCUMENTS

| | | |
|---|---|---|
| 4,669,473 | 6/1987 | Richards et al. . |
| 4,699,271 | 10/1987 | Lincoln et al. . |
| 4,713,076 | 12/1987 | Draenert . |
| 4,738,255 | 4/1988 | Goble et al. . |
| 4,741,330 | 5/1988 | Hayhurst . |
| 4,760,843 | 8/1988 | Fischer et al. . |
| 4,790,304 | 12/1988 | Rosenberg ............... 606/72 |
| 4,828,562 | 5/1989 | Kenna . |
| 4,870,957 | 10/1989 | Goble et al. ............... 606/73 |
| 4,871,289 | 10/1989 | Choiniere . |
| 4,895,148 | 1/1990 | Bays et al. . |
| 4,898,156 | 2/1990 | Gatturna et al. . |
| 4,898,505 | 2/1990 | Froehlich . |
| 4,899,743 | 2/1990 | Nicholson et al. ............... 606/72 X |
| 4,921,383 | 5/1990 | Fischer . |
| 4,927,421 | 5/1990 | Goble et al. . |
| 4,946,468 | 8/1990 | Li ............... 606/72 X |
| 4,968,315 | 11/1990 | Gatturna . |
| 4,969,892 | 11/1990 | Burton et al. . |
| 4,976,680 | 12/1990 | Hayman et al. . |
| 5,002,550 | 3/1991 | Li ............... 606/144 X |
| 5,013,316 | 5/1991 | Goble et al. . |
| 5,015,250 | 5/1991 | Foster . |
| 5,037,422 | 8/1991 | Hayhurst et al. . |
| 5,041,129 | 8/1991 | Hayhurst et al. . |
| 5,046,513 | 9/1991 | Gatturna et al. . |
| 5,053,047 | 10/1991 | Yoon . |
| 5,078,730 | 1/1992 | Li et al. . |
| 5,080,543 | 1/1992 | Murphy . |
| 5,084,050 | 1/1992 | Draenert . |
| 5,085,661 | 2/1992 | Moss . |
| 5,100,417 | 3/1992 | Cerier et al. . |
| 5,102,421 | 4/1992 | Anspach, Jr. . |
| 5,131,533 | 7/1992 | Alpern . |
| 5,144,961 | 9/1992 | Chen et al. . |
| 5,176,682 | 1/1993 | Chow . |
| 5,207,679 | 5/1993 | Li . |
| 5,217,486 | 6/1993 | Rice et al. . |
| 5,258,016 | 11/1993 | DiPoto et al. . |

FOREIGN PATENT DOCUMENTS

| | | |
|---|---|---|
| 2622430 | 10/1987 | France . |
| WO8603666 | 7/1986 | PCT Int'l Appl. . |
| WO8909030 | 10/1989 | PCT Int'l Appl. . |
| WO8910096 | 11/1989 | PCT Int'l Appl. . |
| WO9204874 | 4/1992 | PCT Int'l Appl. . |
| 584855 | 12/1977 | U.S.S.R. . |
| 2084468 | 9/1981 | United Kingdom . |

OTHER PUBLICATIONS lar Repair System", Arthroscopy Equipment and Supplies, Section One, p. 4.

Biomet Inc., "Ligament Screw System", 1990.

Arthrex, The Complete Arthrex Information System.

Mitek Surgical Products, Mitek GII Anchor, High Strength Fixation, 1991.

Mitek Surgical Products, Mitek Anchor System, Effective Soft Tissue Reattachment, 1990.

Mitek Surgical Products, Mitek Quick Anchor, "Fast, Effective, Soft Tissue Reattachment", 1990.

Zimmer, Inc., "STATAK® Soft Tissue Attachment Device", 1988.

Acufex Microsurgical Inc., "TAG® Tissue Anchor Guide System".

Acufex Microsurgical Inc., "Technique for Using the TAG® Tissue Anchor—Rod Style".

Acufex Microsurgical Inc., "Technique for Using the TAG® Tissue Anchor—Wedge Style".

SUTURE ANCHOR INSTALLATION SYSTEM

CROSS REFERENCE TO RELATED APPLICATIONS

The present application is a continuation-in-part of U.S. application Ser. No. 07/898,799 filed Jun. 15, 1992 which is a continuation-in-part of U.S. application Ser. No. 07/673,953 filed Mar. 22, 1991, now abandoned, the disclosures of which are incorporated herein by reference.

BACKGROUND OF THE INVENTION

1. Field of the Invention

The present invention relates to a suture anchor installation system and, more particularly, to a suture anchor installation system comprising a suture anchor insertion tool engaging a two-piece suture anchor having a suture and needle assembly.

2. Discussion of the Related Art

During surgery, it is often necessary to attach muscle tissue or prosthetic implants to bone. Suture anchors are used in the art to facilitate such attachment by securing a suture to bone. Generally, an anchor is implanted into a hole pre-drilled into a bone mass. A suture engaged by the suture anchor extends from the bone and is used to stitch the muscle tissue or prosthetic device to the bone. Suture anchors find particular use in joint reconstruction surgery, especially during attachment of ligaments or tendons to bones in the knee, shoulder, and elbow.

Several systems have been proposed in the art to aid the surgeon in implanting a suture anchor into a bone. One such system, shown in U.S. Pat. No. 5,100,417 to Cerier et al., comprises a driver having a handle and elongated shaft. An anchor snap fits on the end of the shaft over an anti-rotation pin which mates with slots in the anchor. A suture engaged in the anchor has its ends affixed to posts extending from the driver handle. The Cerier et al. system suffers from the disadvantage that the driver does not accommodate sutures having preattached needles. Thus, use of this system requires threading the suture into a needle, a time-consuming procedure for the surgeon.

Another suture anchor installation system is shown in U.S. Pat. No. 5,002,550 to Li. The Li system comprises a suture anchor having a normally curved barb capable of being elastically deformed to a substantially straight configuration. The suture anchor engages a suture having a pair of surgical needles attached to its ends. The installation tool is adapted to receive the surgical needles an a pair of grooves formed in the tool's outer surface. The tool additionally provides a member for selectively covering and uncovering the needles received in the grooves.

The Li suture anchor installation system uses shape-memory alloys to fabricate the suture anchors. Such materials are not bioabsorbable. Additionally, the normally curved barb of the Li system protrudes from the installation tool during positioning of the anchor.

A need exists in the art for a suture anchor installation system composed of a suture anchor insertion tool engaging a suture anchor assembly. The suture anchor assembly should comprise a suture anchor which can be easily implanted yet remain firmly lodged within a pre-drilled hole in bone. At least one surgical needle should be preattached to a suture engaged by the suture anchor. Such a system would provide a site for securely attaching soft tissue or prosthetic devices to bone.

SUMMARY OF THE INVENTION

A suture anchor installation system is provided for securing a suture to bone. The suture can be used to attach soft tissue or a prosthetic device to the bone. As used herein, the term "soft tissue" refers to all of the non-bony tissues within an organism including, but not limited to, muscle, cartilage, skin, tendons, ligaments, etc. The term "prosthetic device" refers to any article implanted in the body including, but not limited to, artificial ligaments, muscles, joints, etc.

The suture anchor installation system of the present invention comprises a suture anchor assembly engaged with a suture anchor insertion tool. The suture anchor assembly features a two-piece suture anchor for insertion into a pre-drilled hole in bone and at least one suture having at least one surgical needle affixed thereto. The two-piece suture anchor comprises a setting pin slidably engaged within an expandable engagement member which grips the sides of the hole. In a preferred embodiment, this engagement member is an expandable rivet. The expandable rivet includes an apertured body portion having at least two barbed legs extending proximally therefrom. The legs are radially expandable in response to proximal movement of the setting pin.

The suture anchor installation system of the present invention further comprises a suture anchor insertion tool. The suture anchor insertion tool includes a body portion and a distally extending shaft portion. An annular region on the distal end of the shaft portion engages rivet legs of the suture anchor while a channel in the shaft portion accommodates the suture.

Needle-retaining assemblies located on the body portion of the suture anchor insertion tool engage the surgical needle or needles attached to the suture. A cover member shields at least part of the body portion of the insertion tool, assisting in retaining the suture.

DETAILED DESCRIPTION OF THE PREFERRED EMBODIMENTS

Figure 1:
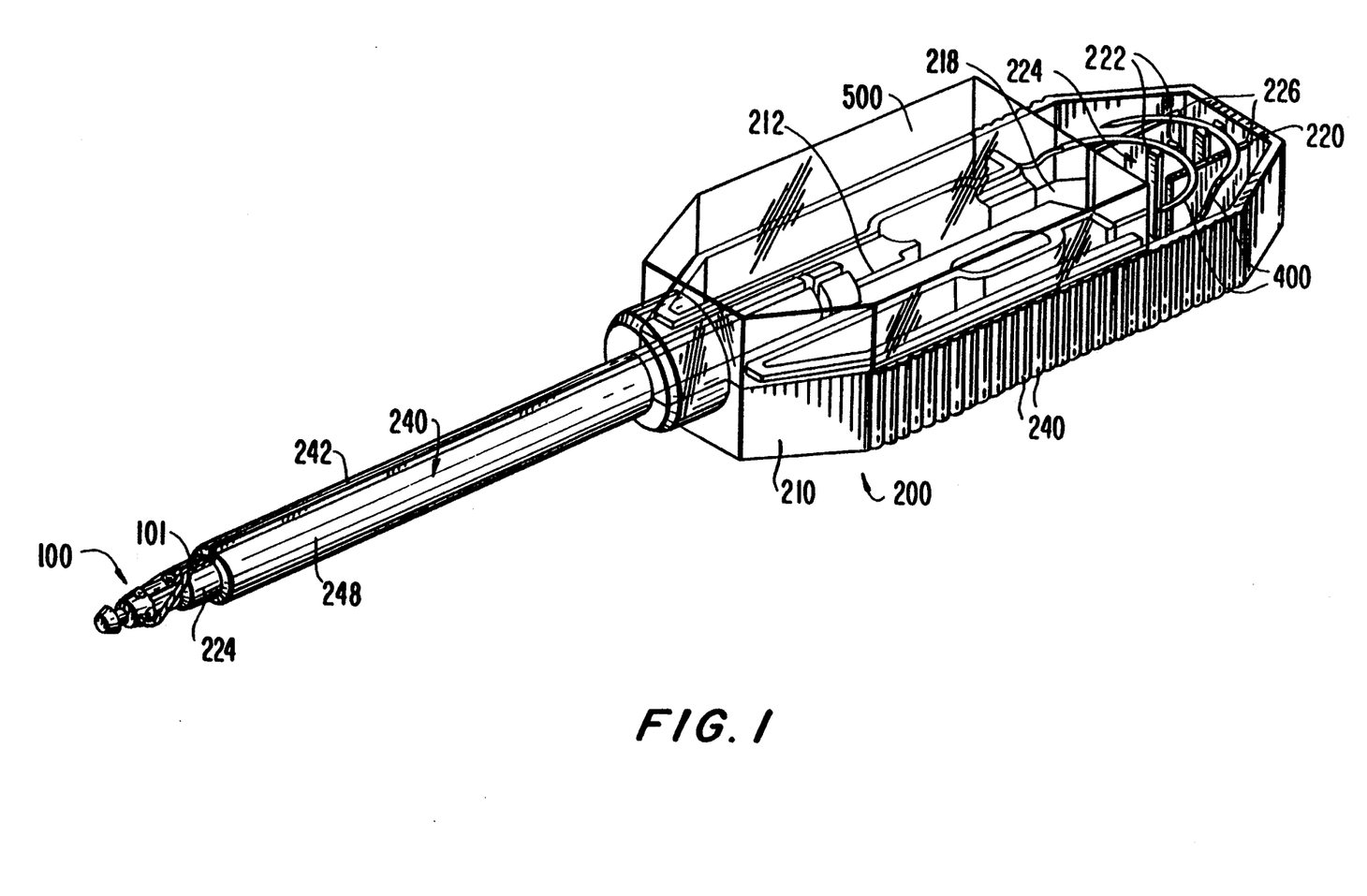
FIG. 1 is a perspective view of the suture anchor installation system of the present invention.
Figure 2:
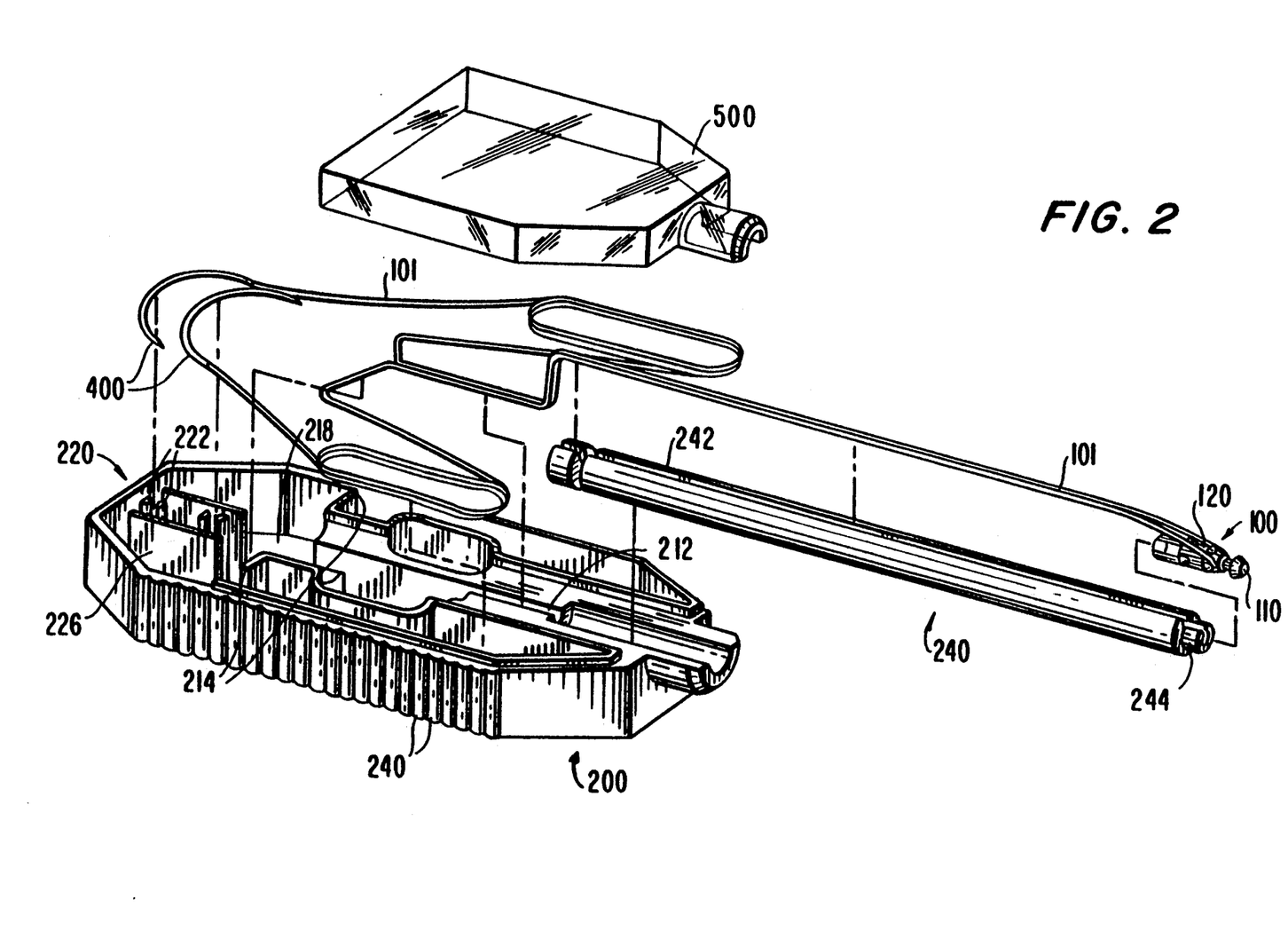
FIG. 2 is a perspective view with the parts separated of the suture anchor installation system of FIG. 1.
Figure 10:
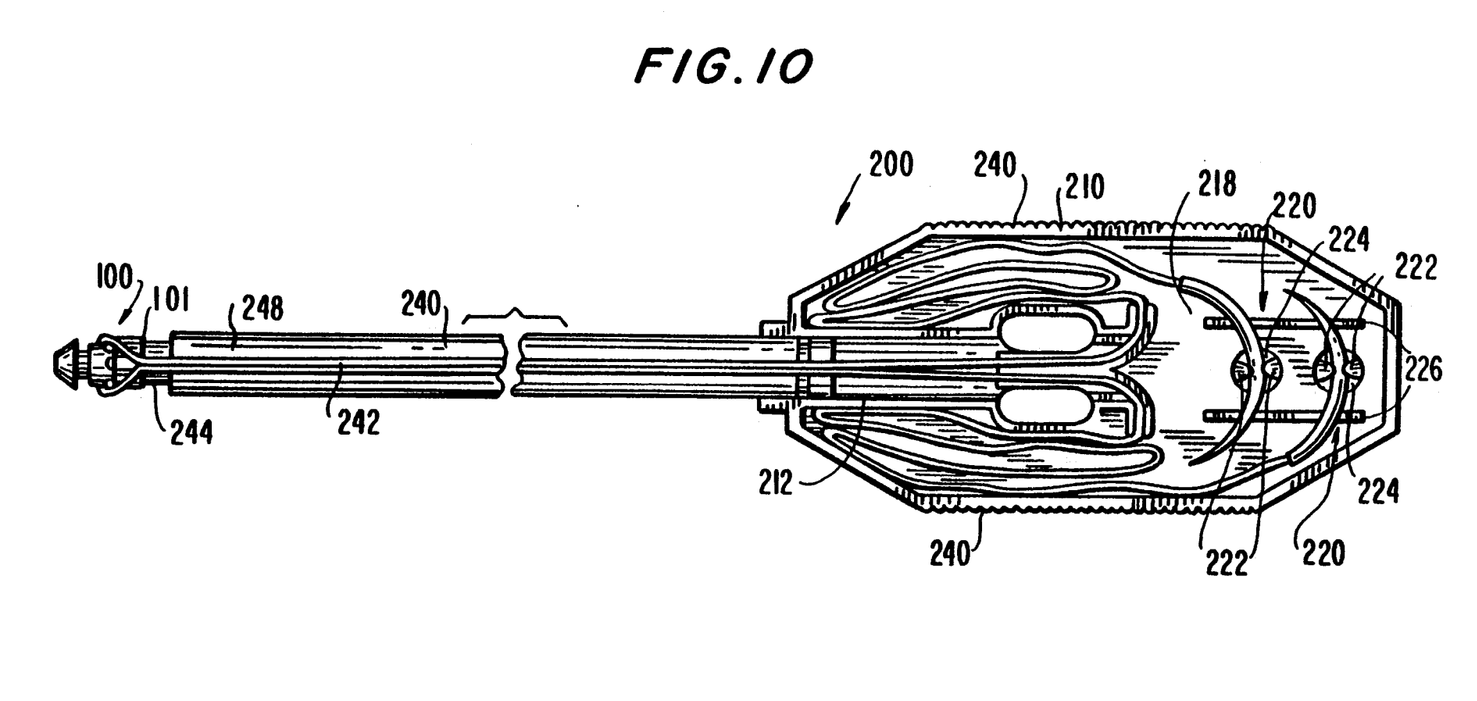
FIG. 10 is a top view in partial cross section of the suture anchor installation system of FIG. 1.

Referring now in specific detail to the drawings, in which like reference numerals identify similar or identical elements throughout the several views, FIGS. 1, 2, and 10 depict a suture anchor installation system according to the present invention. In describing the suture anchor installation system, the term "distal" refers to the direction in which the suture anchor is implanted, i.e., towards the interior of the bone, and the term "proximal" refers to a direction away from the bone and towards the user, opposite to the distal direction. The suture anchor installation system of the present invention comprises a suture anchor assembly 100 engaged with a suture anchor insertion tool 200.

Figure 3:
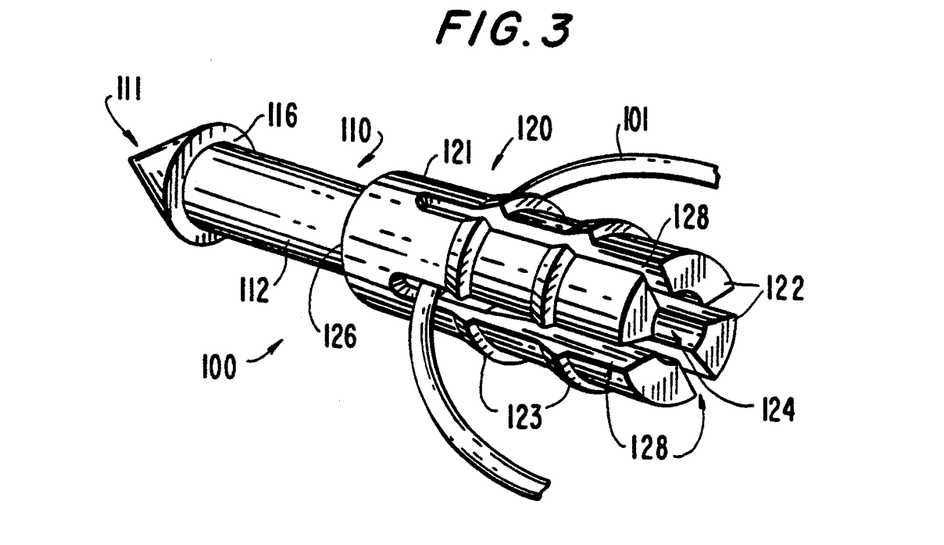
FIG. 3 is a perspective view of a two-piece suture anchor used in the suture anchor installation system.

Suture anchor assembly 100, shown in perspective in FIG. 3, comprises engagement member 120 and setting pin 110. Engagement member 120 is illustratively depicted as an expandable rivet; however, other configurations of engagement member are contemplated. Setting pin 110 is slidably disposed through axial aperture 124 in rivet 120. Setting pin 110 includes distal tip 111, optionally terminating in a sharp point, generally cylindrical body portion 112, proximal end 114, preferably tapered or rounded, and transverse aperture 113 for receiving a suture 101 to be anchored.

Suture 101 is preferably a single, braided suture engaged within setting pin aperture 113 such that each end of suture 101 extends proximally from the suture anchor. The suture may be selected from bioabsorbable or non-absorbable materials, depending upon the desired application. Each end of suture 101 is affixed to a surgical needle 400, as shown in FIGS. 1 and 2. Alternatively, a single end of the suture may be attached to a single surgical needle.

Figure 4:
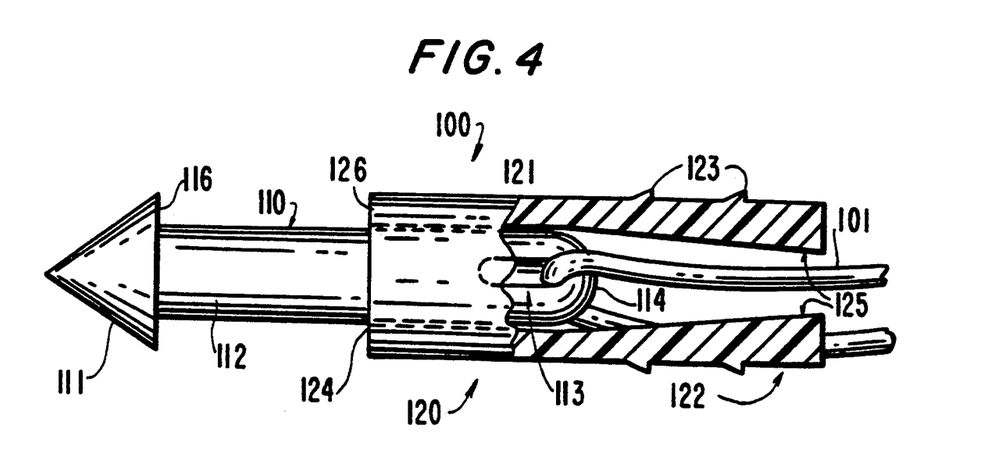
FIG. 4 is a side view of the suture anchor of FIG. 3.

The rivet 120 includes a body portion 121 through which an axial aperture 124 extends for receiving the setting pin 110. Rivet 120 also possesses at least two, and preferably four, legs 122, which extend proximally from the body portion 121. The legs 122 are separated by notches 128 and are resiliently movable in a radial direction, As shown in FIG. 4, each leg 122 has an inner camming surface 125 which tapers towards the axial center of the rivet. Proximal movement of the setting pin 110 causes the proximal end 114 to cam against the inner surface 125 of the leg, urging the leg 122 radially outward. The outer surfaces of the legs are provided with proximally pointing barbs 123 to grip the inner walls of the bore hole in the bone.

The distal end portion 111 of the setting pin has a proximally facing abutment surface 116, and the body portion 121 of the rivet has a distally facing abutment surface 126. Abutment surfaces 116 and 126 cooperate to limit the proximal movement of the setting pin 110 relative to the body portion 121.

An alternate embodiment of the setting pin is illustrated in FIGS. 6, 7, 8, and 9. Setting pin 130 includes a distal tip portion 131 tapering to a flat frontal surface 136, and having a rear, or proximal, abutment surface 136A. Pin 130 further includes a shaft portion 132 and a tapered or rounded proximal or rear portion 134. Shaft portion 132 includes at least one, and preferably two suture accommodating slots 135 extending longitudinally along the sides of the pin 130. A suture accommodating aperture 133 extends transversely to the longitudinal axis of the pin 130 and is located in proximity to the distal end of the pin. The suture can be pre-threaded through aperture 133 and disposed within slots 135 prior to assembly of the pin 130 and rivet 120. Pin 130 can be substituted for pin 110 and is equally suitable for use in conjunction with rivet 120.

In the alternate setting pin 130, the cross-sectional configuration is such that it cooperates with the interior surface of the rivet to prevent rotation of the pin within the rivet. Additionally, slots 135 of the setting pin align with slots 128 of the rivet for ease of suture positioning.

Referring back to FIGS. 1, 2, and 10, suture anchor assembly 100 is insertable by means of suture anchor insertion tool 200. Suture anchor insertion tool 200 comprises a body portion 210 and an elongated shaft portion 240 extending distally from the body portion. Shaft portion 240 has a generally cylindrical shape and includes a suture-retaining channel 242.

At its distal end, the shaft portion terminates in annular region 244. Annular region 244 has an inner diameter slightly less than the outer diameter of rivet legs 122 in their pre-expanded position. The inner diameter of annular region 244 is also less than the diameter of the barbed portion 123 of legs 122. These dimensions permit rivet portion 120 of the suture anchor to be retained within annular region 244 by urging rivet legs 122 inward. The resiliency of legs 122 creates an outward biasing force to frictionally retain the suture anchor within the insertion tool.

Because the diameter of the barbed portion is too large to fit within the insertion tool, only the proximal-most portion of rivet legs 122 are retained within the suture anchor. Thus, the barbed portion provides a proximal end point for insertion of the suture anchor within the shaft portion, ensuring that the suture anchor does not become completely embedded within the insertion tool.

The outer diameter of shaft annular region 244 is smaller than the outer diameter of shaft portion 248 but greater than the diameter of the drilled bone hole. This difference in diameter restricts insertion of the suture anchor installation tool shaft portion 240 beyond annular region 244.

As shown in the embodiment of FIG. 1, suture anchor assembly 100 is oriented within the distal annular region 440 of insertion tool 200 such that a pair of rivet notches 128 is disposed with one notch located on either side of and equidistant from the longitudinal channel 242. Suture 101 extends through both notches of the pair and into the longitudinal channel 242 of the shaft. However, the suture anchor assembly 100 may be oriented in other positions on the distal end of insertion tool 200.

Body portion 210 of the suture anchor insertion tool comprises a suture-retaining channel 212 aligned with channel 242 of the shaft portion. At the proximal end of channel 212, suture-retaining tabs 214 grip each end of suture 101. Tabs 214, fabricated from a resilient material, are displaced during assembly, exerting a biasing spring-back force to compress the suture. Tabs 214 clamp suture 101 with enough force to allow the suture to be tensioned during assembly. This tension is sufficient to aid in retaining setting pin 110 within rivet 120 of the suture anchor assembly.

The respective ends of suture 101 are guided by channels 214 towards either side of suture anchor insertion tool 200. Suture 101 is retained within the body portion of the insertion tool, each end optionally coiled depending upon the length of suture required for the particular application.

To aid in retention of the suture, a canopy-like cover member 500 extends over at least a part of the body portion of the insertion tool. It is contemplated that the cover member may, in alternate embodiments, cover the entire body portion of the instrument, and/or the cover member may be slidable along the longitudinal axis. Alternatively, the insertion tool may be used without a cover member. In such an embodiment, additional suture retention members may be provided, such as posts around which the suture may be coiled.

The body portion of the suture anchor insertion tool further includes a pair of needle-retaining assemblies 220 for engaging surgical needles 400. Needle-retaining assemblies 220 comprise a pair of semi-circular needle-engaging clips 222 protruding from cavities 224. A pair of needle-supporting rails 226 maintains needles 400 in an elevated position with respect to surface 218 of the insertion tool body portion. The combination of raised support rails 226 and cavities 224 allows the user to easily grasp the surgical needles 400 with a needle-gripping instrument.

The needle-engaging clips may include a laterally-projecting portion (not shown) to further assist in retaining the needles. Clips 222 are dimensioned and configured to engage the concave surface of the needle at a single point and to engage the convex surface of the needle at a single point.

The body portion of the suture anchor insertion tool additionally includes ridges 240 disposed on the sides of the body portion 210 to aid the user in gripping the tool during suture anchor placement.

Figure 5:
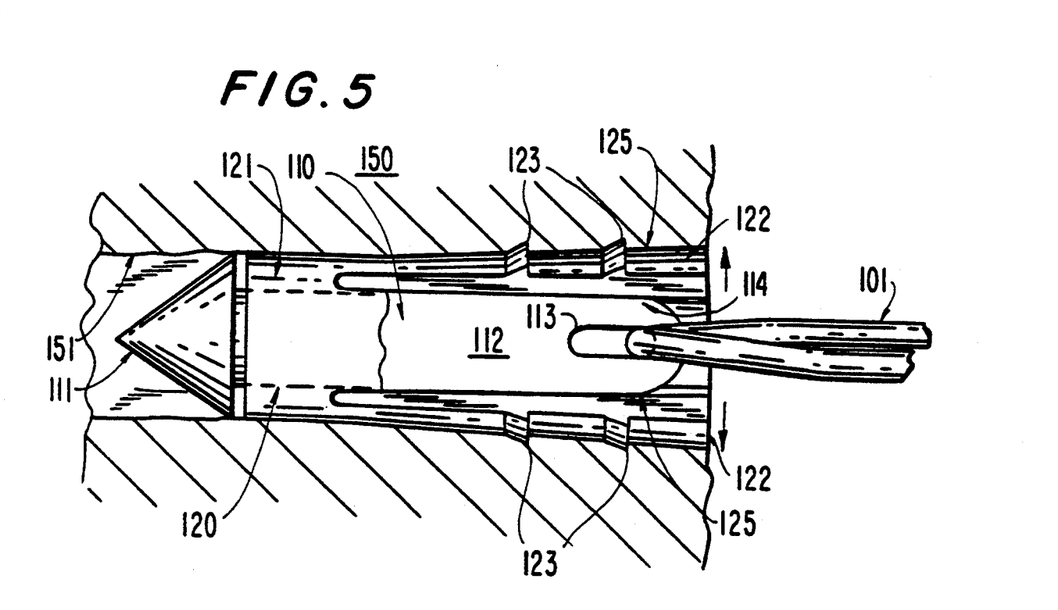
FIG. 5 is a side view of the suture anchor of FIG. 3 showing the suture anchor in its expanded condition implanted in bone.
Figure 6:
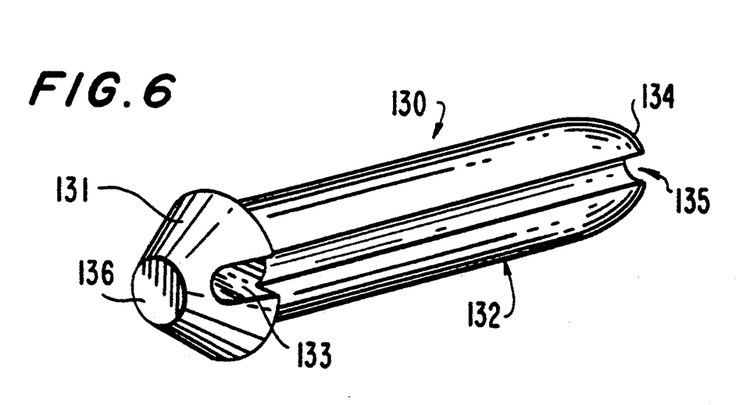
FIG. 6 is a perspective view of another embodiment of the setting pin of the suture anchor.
Figure 7:
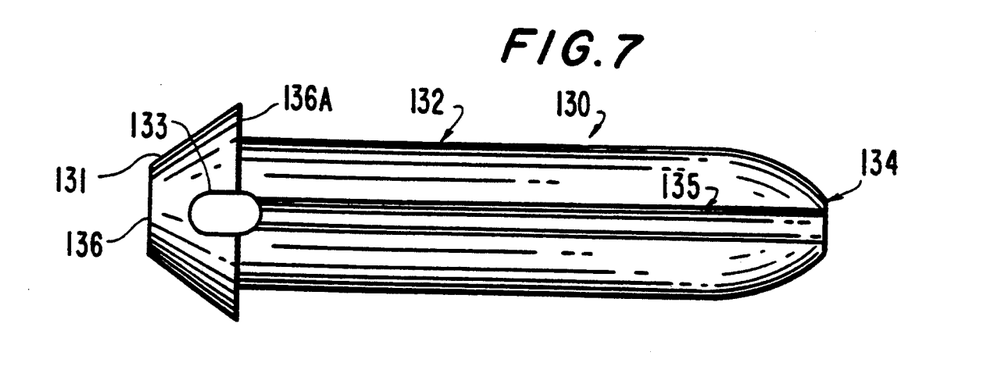
FIG. 7 is a side view of the setting pin of FIG. 6.
Figures 8, 9:
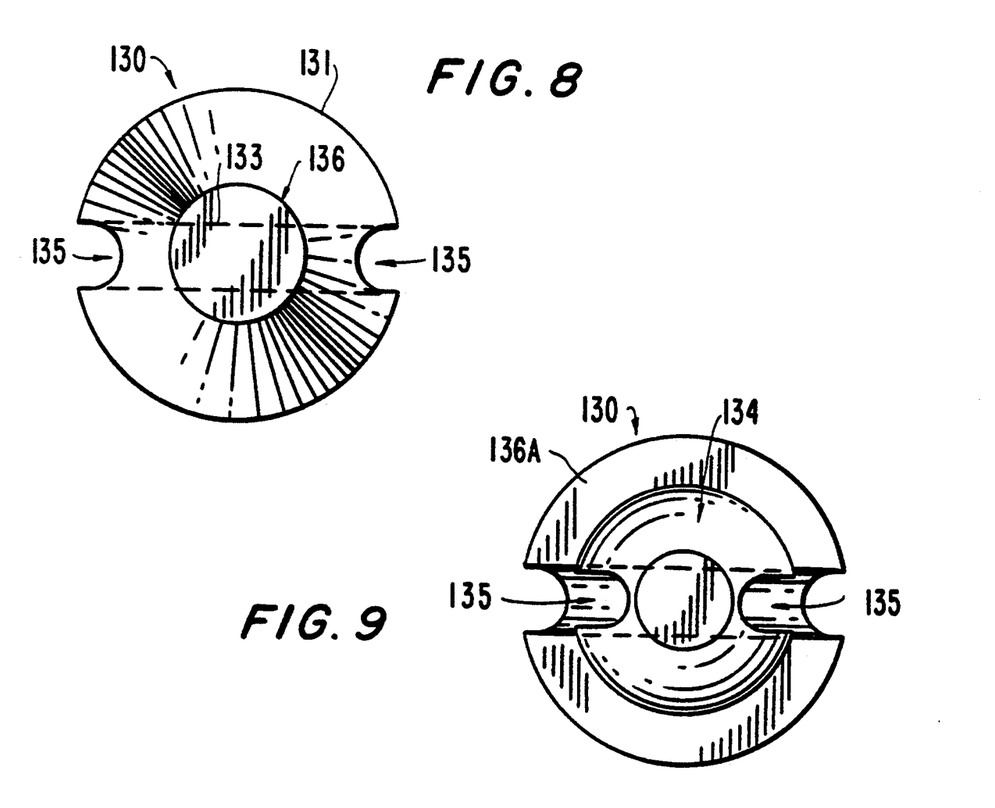
FIG. 8 is a front end view of the setting pin of FIG. 6.
FIG. 9 is a rear end view of the setting pin of FIG. 6.

To use the suture anchor installation system of the present invention, a hole 151 is drilled in bone 150, as shown in FIG. 5. The diameter of the hole is selected to be slightly larger than the diameter of the suture anchor rivet 120 in its pre-expanded condition. The suture anchor installation system is delivered to the site of the drilled hole with suture anchor 100 engaged in the distal end of the shaft portion of the insertion tool 244, as depicted in FIG. 1. Optionally, delivery of the suture anchor installation system is accomplished arthroscopically, the shaft portion of the insertion tool being capable of passing through a cannula.

In the configuration of FIG. 1, the setting pin 110 is slidably disposed through aperture 124 in rivet 120. The suture 101 to be fastened is disposed through lateral aperture 113 in the setting pin. In the "inactivated" configuration, the setting pin 110 is in a position such that it is relatively distally advanced with respect to the rivet 120.

The suture anchor 100 is distally advanced by insertion tool 200 into the bore hole 151 in bone 150. Because the diameter of region 248 of the shaft portion is greater than that of bore hole 151, insertion tool 200 may not be advanced beyond annular region 244, i.e., the insertion depth of the tool is self-limiting. Because the length of the annular region corresponds to a predetermined position of the anchor within bore hole 151, optimal insertion of suture anchor assembly 100 is assured. Insertion tool 200 is removed from the bore hole following positioning of the suture anchor.

To set the suture anchor, the setting pin 110 is moved proximally with respect to the rivet 120. This may be accomplished by pulling the suture 101, whereupon the proximal end 114 of the setting pin cams against the inner surfaces 125 to urge legs 122 radially outward, as illustrated in FIG. 5. Barbs 123 then frictionally engage the walls of the bore hole and resist proximal movement of the rivet 120. Thus, suture anchor 100 is locked into place for firmly securing the suture 101.

When the setting pin 110 is moved to its most proximal position with respect to the rivet 120, surfaces 116 and 126 abut each other and thereby prevent the setting pin from being pulled proximally out of the rivet 120 by pulling force exerted on the suture 101. Tension exerted on the suture 101 serves to more tightly lodge the suture anchor 100 within bore hole 151.

Once the suture anchor is set within the bore hole, needles 400 are removed from needle retaining assemblies 220. Suturing of soft tissue or a prosthetic device to the bone can then be performed using known techniques.

The suture anchor is preferably fabricated from a flexible and resilient material with a strength sufficient for the purposes described herein. Preferably, the suture anchor is fabricated from bioabsorbable materials such as homopolymers and copolymers of glycolide, lactide, dioxanone, caprolactone, trimethylene carbonate, and mixtures thereof, The body portion 210 of the suture anchor insertion tool may be fabricated from any lightweight material capable of providing the necessary strength and rigidity for anchor insertion. In particular, lightweight plastics such as LEXAN TM polycarbonate are contemplated, Shaft portion 240 of the suture anchor insertion tool is fabricated from material with sufficient strength and bending and torsional rigidity to withstand insertion. Metals such as non-corrosive stainless steels, structural plastics, and polymeric composites are suitable materials.

The suture anchor installation system of the present invention has the significant advantage of providing an easy, time saving technique and device for soft tissue attachment to bone. The suture anchor component advantageously provides a self-tightening means of anchorage. This active means of anchorage is designed to provide greater resistance to pull out as the tension on the suture increases. The device provides sufficient anchoring strength to allow repair to occur concurrently with a partial return to full function. In use, the device is primarily subjected to tensile forces and provides adequate strength to stabilize the reattached soft tissue. By fabricating the device out of a biodegradable material, the device is capable of providing full initial anchorage strength, and, with time, allows for gradual load sharing with the repaired tissue. This load sharing capability may be the optimal means for achieving full repair and restoration of function. Another advantage is that the resorbable material will eventually be replaced by natural tissue.

The insertion tool of the suture anchor installation system is uniquely adapted to deliver the two-piece suture anchor. The distal annular region of the shaft portion, in cooperation with the suture-retaining channels in the shaft and body portions of the insertion tool and the gripping tabs, retains the suture with sufficient tension to assist in maintaining the setting pin of the suture anchor in engagement with the suture anchor rivet during insertion of the suture anchor. The configuration of the needle-retaining assemblies permits the user to easily grasp a needle during use through the combination of the needle-supporting rails and the needle-engaging clips.

While the invention has been particularly shown and described with reference to the preferred embodiments, it will be understood by those skilled in the art that various modifications and changes in form and detail may be made without departing from the scope and spirit of the invention. Accordingly, modifications such as those suggested above, but not limited thereto, are to be considered within the scope of the invention.

What is claimed is:

1. A suture anchor insertion tool comprising:

a body portion having proximal and distal ends;

an elongated shaft portion having proximal and distal ends extending distally from a distal end of said body portion, the distal end of said shaft portion including a projecting annular portion for engaging a two-piece suture anchor comprising a setting pin engaged within engagement means and having at least one suture operatively associated therewith;

a channel extending the length of said elongated shaft portion, said channel receiving a portion of the at least one suture extending from the suture anchor;

at least one needle-retaining assembly, said needle-retaining assembly comprising a pair of needle-retaining projections extending from said body portion; and a suture-retaining member positioned on the body portion of said suture anchor insertion tool, said suture-retaining member including suture-retaining tabs to grip the at least one suture extending from the suture anchor to maintain the setting pin within the engagement means of the two-piece suture anchor.

2. A suture anchor insertion tool according to claim 1 wherein said suture anchor insertion tool comprises a pair of needle-retaining assemblies.

3. A suture anchor insertion tool according to claim 1 wherein said needle-retaining assembly further comprises first and second rails extending from said body portion, said first and second rails being disposed adjacent said needle-retaining projections such that a needle engaged in said needle-retaining projections is at least partially supported on said first and second rails.

4. A suture anchor insertion tool according to claim 1 further comprising a cover member cooperating with said body portion of said suture anchor insertion tool to enclose at least a portion thereof.

5. A suture anchor installation system comprising:

a suture anchor insertion tool comprising a body portion having proximal and distal ends and an elongated shaft portion having proximal and distal ends, said shaft portion extending distally from a distal end of said body portion;

a suture anchor assembly held by a distal end of said shaft portion, said assembly comprising a suture anchor having engagement means for insertion into a hole in bone and a setting-pin engaged within said engagement means, said engagement means including a body portion having a distal end and an axially extending aperture, and at least two legs extending proximally from said body portion, said legs being expandable in response to proximal movement of said setting pin, said setting pin being slidable within said axially extending aperture to expand said legs and having means for engaging a suture;

at least one suture operatively associated with said suture anchor setting pin;

at least one surgical needle attached to said at least one suture;

a needle-retaining assembly provided in said body portion of said insertion tool to receive said at least one surgical needle; and means cooperating with said insertion tool body portion for retaining said at least one suture with sufficient tension to maintain said setting pin within said engagement means.

6. A suture anchor installation system according to claim 1 wherein the suture anchor is fabricated from bioabsorbable material.

7. A suture anchor installation system according to claim 6 wherein said bioabsorbable material is a polymer selected from the group consisting of homopolymers and copolymers of glycolide, lactide, caprolactone, dioxanone, trimethylene carbonate and mixtures thereof.

8. A suture anchor installation system according to claim 5 wherein said needle-retaining assembly comprises a pair of needle-retaining projections extending from said body portion of said suture anchor insertion tool.

9. A suture anchor installation system according to claim 5 wherein said suture anchor further comprises at least one barb on the outer surface of each of said at least two legs of said engagement means.

10. A suture anchor installation system according to claim 5 further comprising channel means extending the length of said elongated shaft portion, said channel means being adapted to receive said at least one suture extending from said suture anchor.

11. A suture anchor installation system according to claim 5 wherein said needle-retaining assembly further comprises first and second rails extending from said body portion, said first and second rails being disposed adjacent said needle-retaining projections such that a needle engaged in said needle-retaining projections is at least partially supported on said first and second rails.

12. A suture anchor installation system according to claim 5 further comprising a cover member cooperating with said body portion of said suture anchor insertion tool to enclose at least a portion thereof.

13. A suture anchor installation system according to claim 5 wherein said at least one suture comprises a single, bioabsorbable suture having first and second ends, said suture being positioned within said suture-engaging means such that said first and second ends extend proximally from said suture anchor.

14. A suture anchor installation system according to claim 13 wherein said first and second ends of said suture are respectively attached to first and second surgical needles.

15. A suture anchor installation system according to claim 5 wherein said suture anchor insertion tool further comprises a pair of needle-retaining assemblies.

* * * * *